(12) United States Patent
Butler et al.

(10) Patent No.: US 8,636,779 B2
(45) Date of Patent: Jan. 28, 2014

(54) SPINE PLATE WITH CONFIGURED BONE SCREW BORES

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 1167 days.

(21) Appl. No.: 12/072,485

(22) Filed: Feb. 26, 2008

(65) Prior Publication Data

US 2008/0208263 A1 Aug. 28, 2008

Related U.S. Application Data

(60) Provisional application No. 60/903,499, filed on Feb. 26, 2007.

(51) Int. Cl.
*A61B 17/80* (2006.01)
(52) U.S. Cl.
USPC ............................ 606/280; 606/286; 606/291
(58) Field of Classification Search
USPC .................................. 606/280, 286, 289, 291
See application file for complete search history.

(56) References Cited

U.S. PATENT DOCUMENTS

| 6,342,055 B1 | 1/2002 | Eisermann et al. | |
| 2002/0077630 A1* | 6/2002 | Lin | 606/69 |
| 2004/0097935 A1 | 5/2004 | Richelsoph et al. | |
| 2005/0004574 A1 | 1/2005 | Muckter | |
| 2005/0131413 A1* | 6/2005 | O'Driscoll et al. | 606/73 |
| 2005/0137597 A1 | 6/2005 | Butler et al. | |
| 2005/0149026 A1 | 7/2005 | Butler et al. | |
| 2005/0277937 A1* | 12/2005 | Leung et al. | 606/69 |
| 2006/0229618 A1 | 10/2006 | Dube | |
| 2006/0276793 A1* | 12/2006 | Berry | 606/69 |
| 2008/0147125 A1 | 6/2008 | Colleran et al. | |

FOREIGN PATENT DOCUMENTS

| WO | WO 2004/017837 A2 | 3/2004 |
| WO | WO 2008/106105 A2 | 9/2008 |

OTHER PUBLICATIONS

International Search Report and Written Opinion for PCT/US2008/002486, mail date Jul. 25, 2008, 5 pages.

* cited by examiner

*Primary Examiner* — Nicholas Woodall
*Assistant Examiner* — Christine Nelson
(74) *Attorney, Agent, or Firm* — Foley & Lardner LLP

(57) ABSTRACT

A single to multi-level spine plate has configured bone screw bores that cooperate with bone screws to retain a bone screw in a determinative position. In one form, the determinative position is a self-capture position wherein the bone screw is retained without the aid of any additional bone screw retention device. In another form, the determinative position is a limited angulation orientation of a bone screw relative to the spine plate. This limited angulation may be different for end plate bone screw bores than for middle plate bone screw bores. The bone screw bores may be configured to prohibit angulation once set. In another form, the determinative position is the reception of a cooperating bone screw at a centroid of the bone screw bore when installed.

23 Claims, 15 Drawing Sheets

SPINE PLATE WITH CONFIGURED BONE SCREW BORES

RELATED APPLICATIONS

This patent application claims the benefit of and/or priority to U.S. Provisional Patent Application No. 60/903,499 filed Feb. 26, 2007, entitled "Spine Plates, Bone Screws and Spine Plate Constructs" the entire contents of which is specifically incorporated by reference.

BACKGROUND OF THE INVENTION

1. Field of the Invention

The present invention relates generally to devices for the internal fixation of the spine particularly within the fields of orthopedics and/or neurosurgery such as spinal implants for holding vertebral bones fixed relative to one another and, more particularly, to static bone fixation implants for use in spinal surgical procedures for stabilizing the relative motion of, temporarily or permanently immobilizing, bones of the spine.

2. Background Information

Spine plates have been used for more than 20 years to increase spine stability following single and multi-level spine surgery. Plates implanted during surgery for reasons such as disease, trauma, defect, accident or the like, are used to stabilize one or more spinal vertebrae. Stabilization leads to a proper healing or a desired outcome. The plate is mounted to one or more vertebrae during the surgery. Typically, bone screws are used to mount the plate to the one or more vertebrae. It is important during the mounting process that the plate be properly aligned on the vertebrae for receipt of the mounting screws.

In some instances, it is desirous to cause the fusion of two adjacent vertebrae. If this is the case, the surgeon makes an incision to reach the spine. Tissues and muscles are retracted (spread apart) to reveal the proper level in the spine. The cartilaginous material or disc between the two vertebrae is removed and the bone surface abraded to encourage a bleeding surface. Blood from the bleeding surfaces is desired in order for the bones to fuse. The space between the adjacent vertebrae is filled with bone graft. A plate is then screwed into the superior (top) and inferior (bottom) vertebrae. This stabilizes the spine to facilitate fusion and healing.

In all cases, the spine plates must be fastened to the vertebrae. This is accomplished by bone screws. The bone screws are received in bores of the spine plate and hold the spine plate to the vertebra. In order to prevent anti-rotation or "backing out" of the bone screw once it has been rotated into the bone (vertebra), caps or prong structures are placed into drive sockets in the heads of the bone screws. This detrimentally adds an extra component to the plate assembly or construct. It would be desirable to provide a spine plate and/or spine plate assembly that eliminates this extra component.

Moreover, bone screw bores of current spine plates do not have the configuration or geometry to allow angulation of bone screws as appropriate or to prohibit angulation of bone screws as appropriate while providing a positive retention of the bone screw by the plate alone. It would be desirable to provide a spine plate and/or spine plate assembly having bone screw bores that are configured to provide for angulation of a bone screw and/or the prohibition of angulation of a bone screw as appropriate while providing a positive retention of the bone screw by the plate alone.

Other objects will become apparent from the following.

SUMMARY OF THE INVENTION

A single to multi-level spine plate has configured bone screw bores that cooperate with bone screws to retain a bone screw in a determinative position.

In one form, the determinative position is a self-capture position wherein the bone screw is retained without the aid of any additional bone screw retention device or solely by bone screw bore geometry. Without limitation, the self-capture feature may be implemented via undercuts in lips of the bone screw bores of the spine plate. Bone screws may include corresponding lips that cooperate with the undercuts to achieve self-capture thereof.

In another form, the determinative position is a limited angulation orientation of a bone screw relative to the spine plate. This limited angulation may be different for end plate bone screw bores than for middle plate bone screw bores. In an embodiment of this form, a bone screw bore has geometry that cooperates with a bone screw to provide for a limited range of bone screw angulation in the cephalad to caudal direction for end plate bone screw bores. Such may be thirty degrees (30°) of angulation in the cephalad to caudal direction. In another embodiment of this form, a bone screw bore has geometry that cooperates with a bone screw to provide for a limited range of bone screw angulation in the medial to lateral direction for middle plate bone screw bores. Such may be ten degrees (10°) of angulation in the medial to lateral direction. The bone screw bores may be configured to prohibit angulation once set.

In another form, the determinative position is the reception of a cooperating bone screw at a centroid of the bone screw bore when installed. In one embodiment of this form, the bone screw bores have an annular sidewall that is spherically cupped (having an egress that is axially offset or skewed from an opening of the bone screw bore). A cylindrical opening to the bone screw bore provides for angulation of a screw head by such geometry.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Like reference numerals indicate the same or similar parts throughout the several figures.

Figure 1:
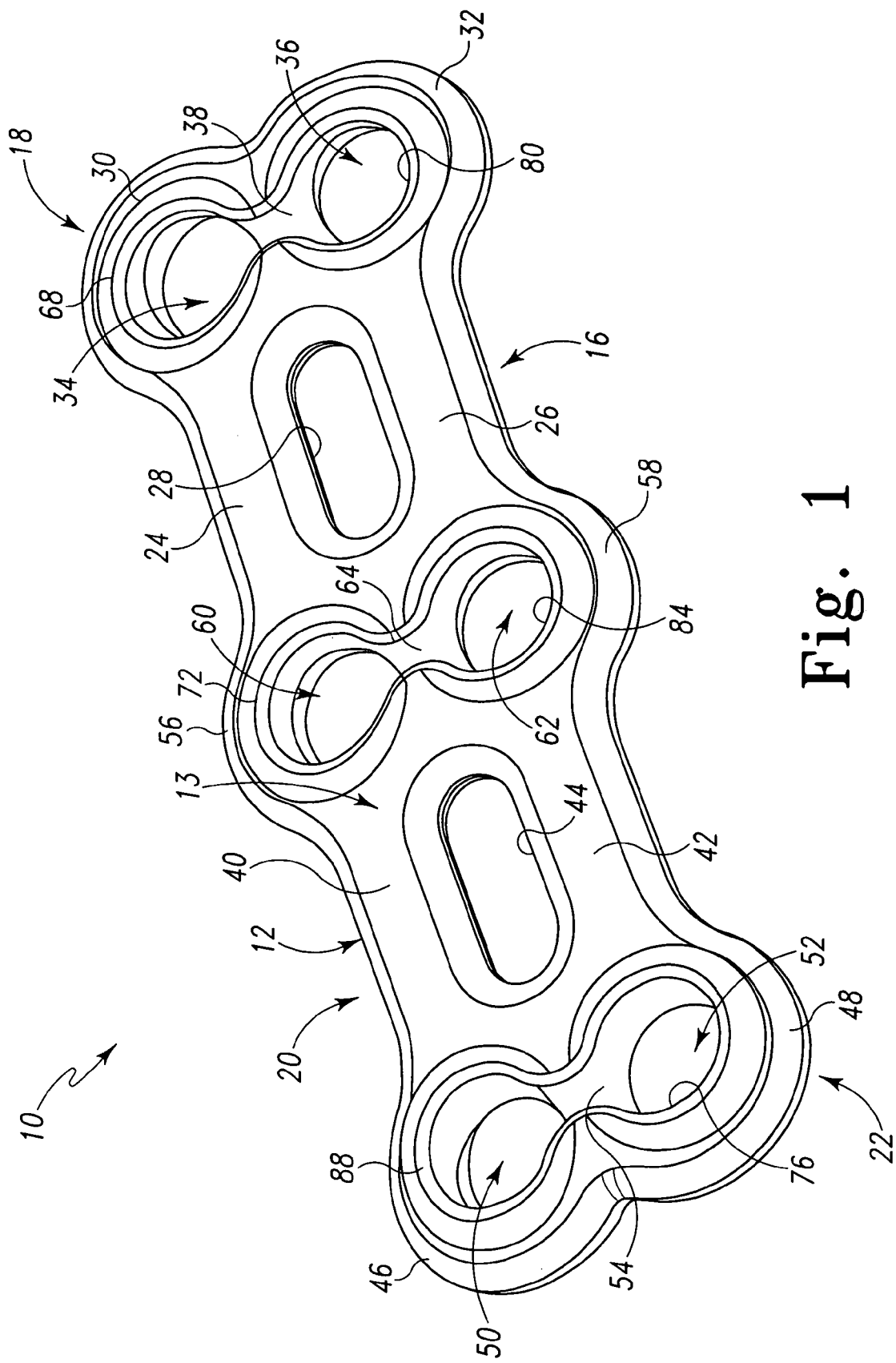
FIG. 1 is an anterior perspective view of an exemplary embodiment of a two level (2-L) spine plate fashioned in accordance with the present principles.
Figure 2:
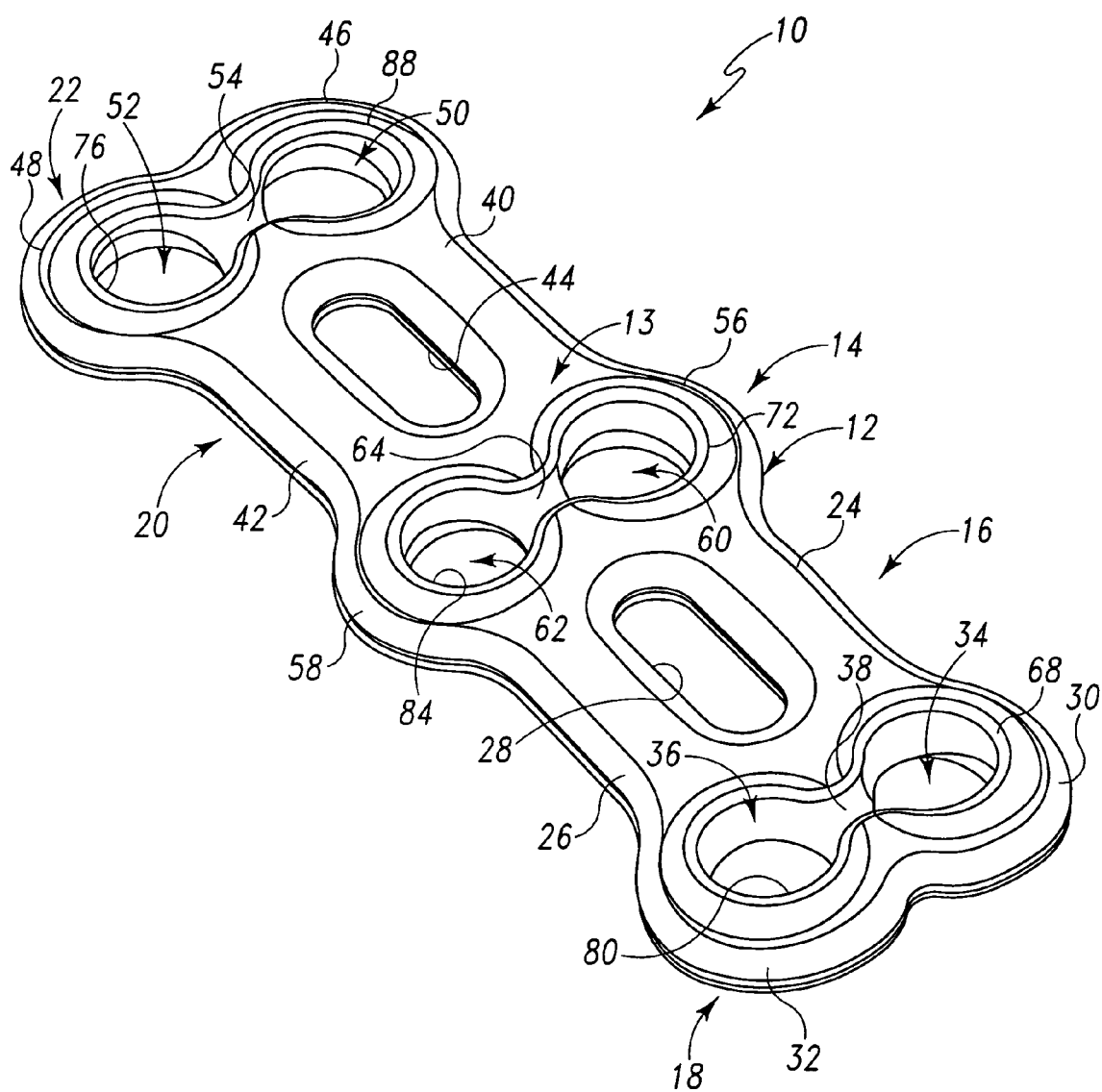
FIG. 2 is another anterior perspective view of the 2-L spine plate of FIG. 1.
Figure 3:
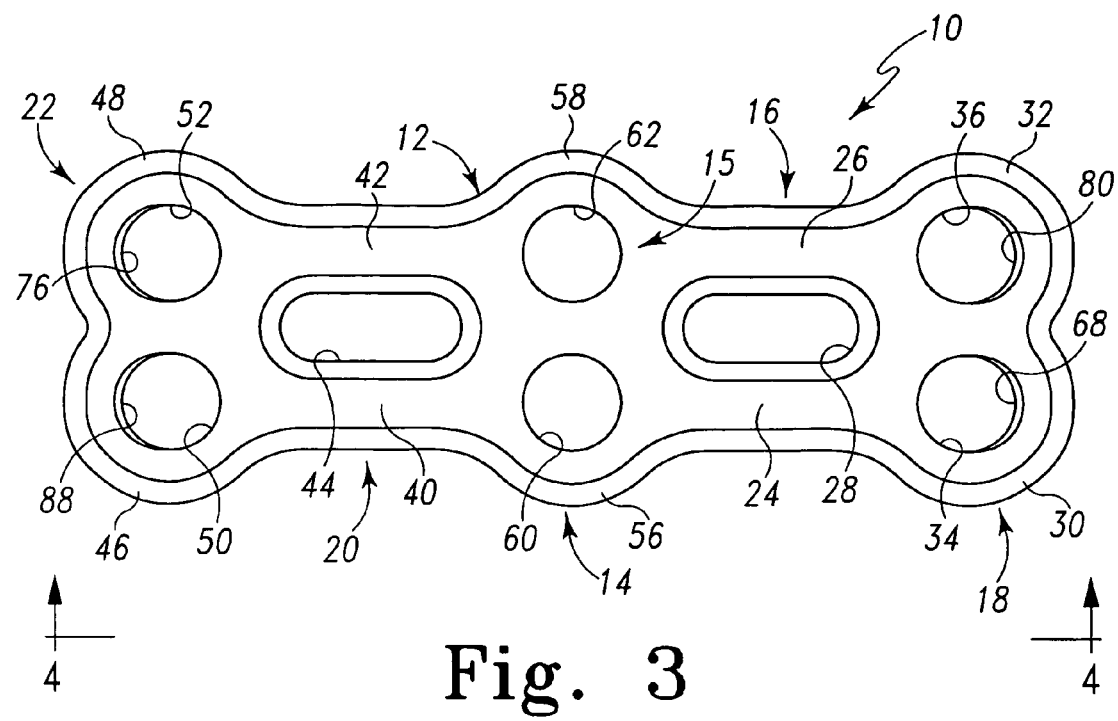
FIG. 3 is a posterior plan view of the 2-L spine plate of FIG. 1.
Figure 4:
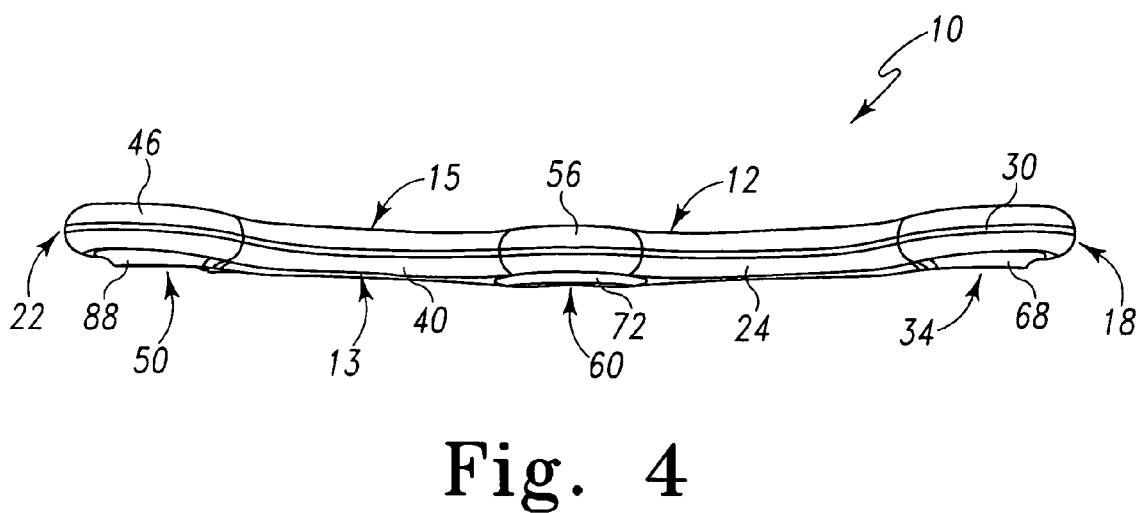
FIG. 4 is a side view of the 2-L spine plate of FIG. 3 taken along line 4-4 thereof.
Figure 6:
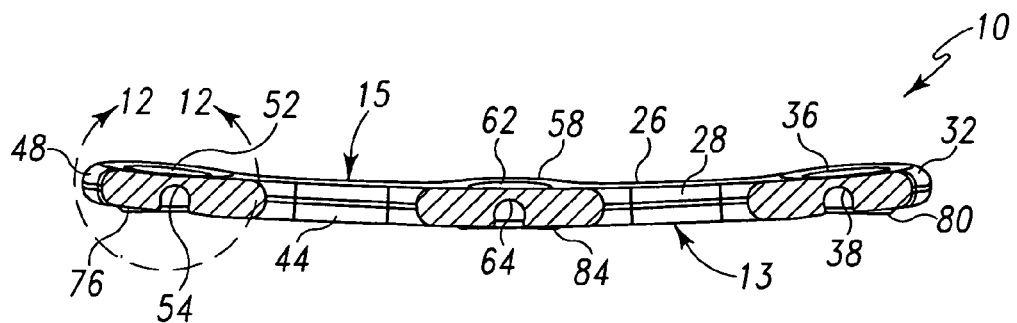
FIG. 6 is a sectional view of the 2-L spine plate of FIG. 5 taken along line 6-6 thereof.
Figure 5:
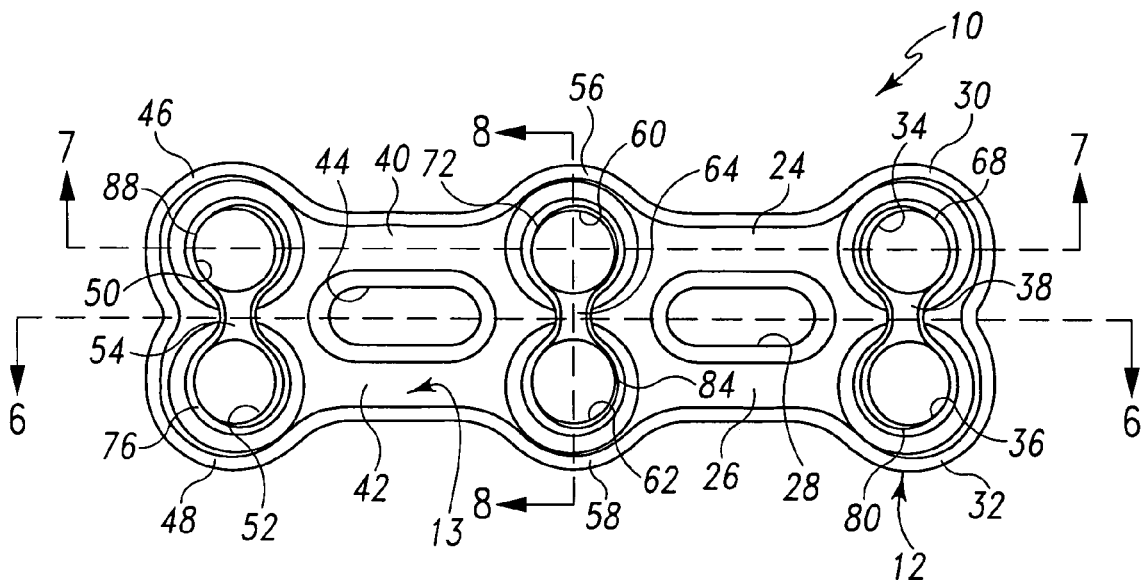
FIG. 5 is an anterior plan view of the 2-L spine plate of FIG. 1.

A description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE PREFERRED EMBODIMENTS

Referring to the figures and particularly to FIGS. 1-12, there is depicted an embodiment of a two-level (2-L) spine or spinal plate generally designated 10 fashioned in accordance with the present principles. Single level and multiple level (up to five levels) spine plates are also contemplated that utilize the present principles. It should be understood that the 2-L spine plate 10 is representative of all such plates. These plates are adapted and/or configured to be placed onto vertebrae of the spine. The 2-L spine plate 10 is formed of a suitable biocompatible material such as titanium, stainless steel, alloys thereof, and other biomaterials.

The 2-L spine plate 10 is defined by a body 12 having an anterior 13 and a posterior side 15. The body 12 is formed of a middle section 14, a first neck 16 extending from one side of the middle section 14 and terminating in a first end 18 distal the middle section 14, and a second neck 20 extending from another side of the middle section 14 and terminating in a second end 22 distal the middle section 14. It should be appreciated that the terms first and second are arbitrary unless indicated otherwise. As best discerned in FIGS. 4 and 6-9, the plate body 12 is curved or arched from end 18 to end 22 (along a saggittal plane). The plate body 12 may be made in various sizes.

The first neck 16 has a first opening or window 28 formed between the middle section 14 and the first end 18 and is preferably oval as shown, but may be other shapes as desired. The first opening 28 forms a graft window of and for the plate 10 and defines first and second neck portions 24 and 26 of the first neck 16. The first neck portion 24 of the first neck 16 extends from one side of a first side boss 56 of the middle section 14 to a first end boss 30 of the first end 18. The second neck portion 26 of the first neck 16 extends from one side of a second side boss 58 of the middle section 14 to a second end boss 32 of the first end 18. The second neck 20 has a second opening or window 44 formed between the middle section 14 and the second end 22 and is preferably oval as shown, but may be other shapes as desired. The second opening 44 forms a graft window of and for the plate 10 and defines first and second neck portions 40 and 42 of the second neck 20. The first neck portion 40 of the second neck 20 extends from another side of the first side boss 56 of the middle section 14 to a first end boss 46 of the second end 22. The second neck portion 42 of the second neck 20 extends from another side of the second side boss 58 of the middle section 14 to a second end boss 48 of the second end 22.

Figure 7:
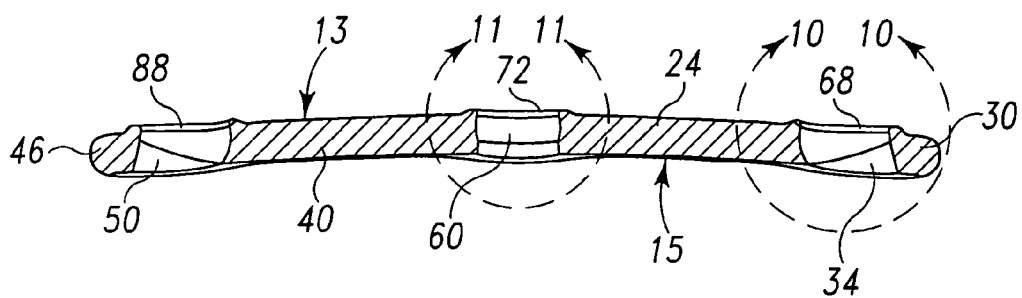
FIG. 7 is a sectional view of the 2-L spine plate of FIG. 5 taken along line 7-7 thereof.
Figure 8:
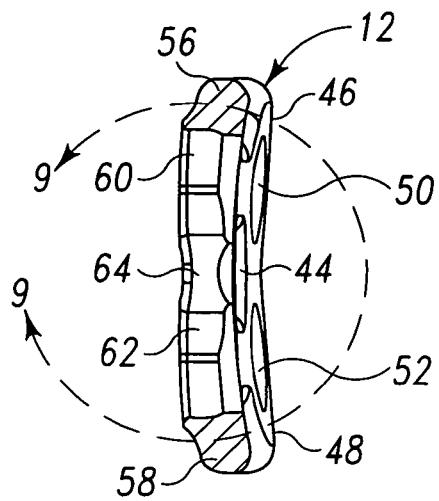
FIG. 8 is a sectional view of the 2-L spine plate of FIG. 5 taken along line 8-8 thereof.
Figure 9:
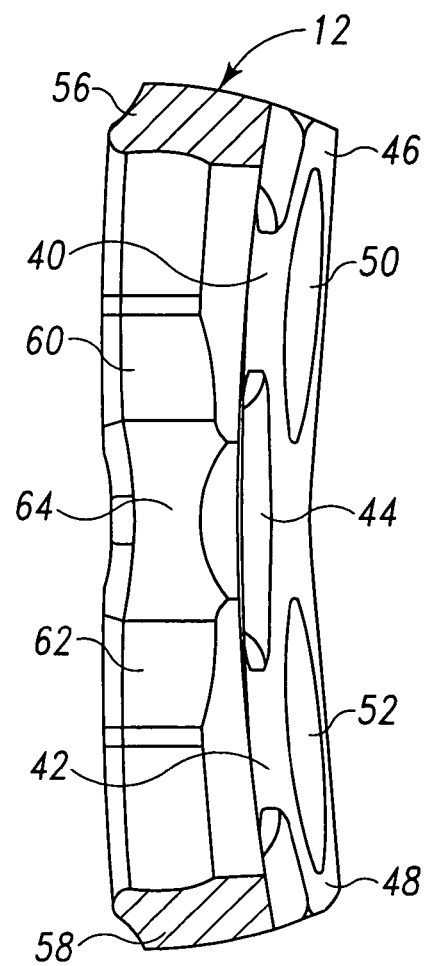
FIG. 9 is an enlarged portion of the sectional view of FIG. 8 taken along circle 9-9 thereof.
Figure 10:
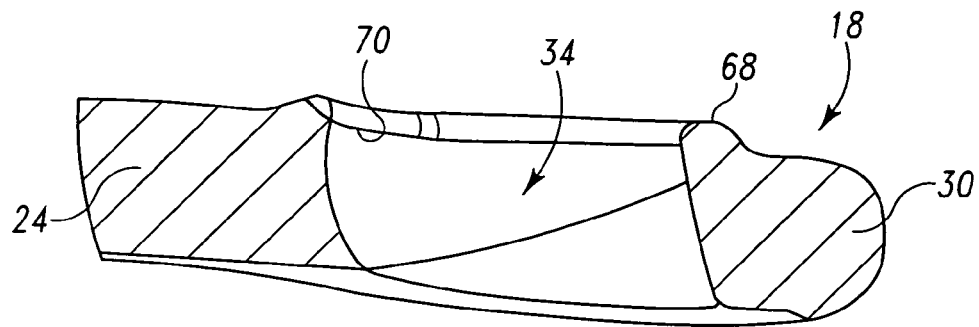
FIG. 10 is an enlarged portion of the sectional view of FIG. 7 taken along circle 10-10 thereof.
Figure 11:
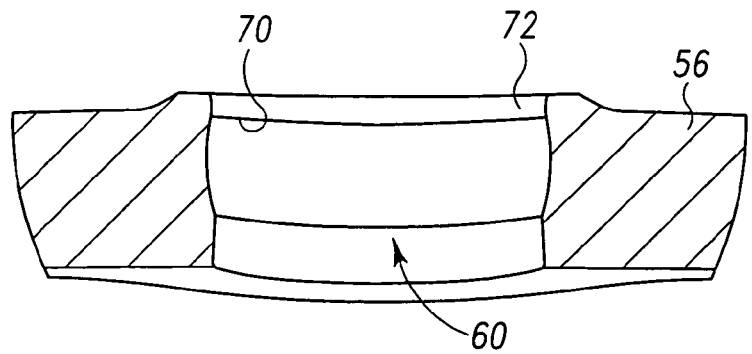
FIG. 11 Is an enlarged portion of the sectional view of FIG. 7 taken along circle 11-11 thereof.
Figure 25:
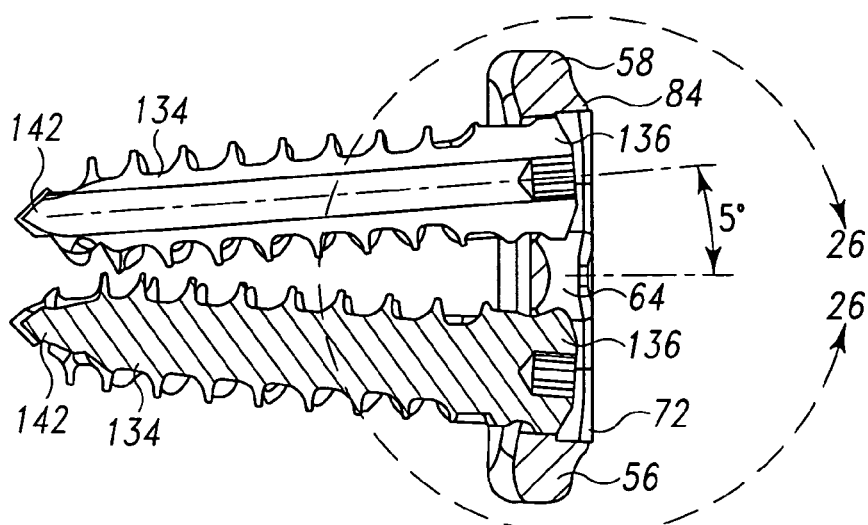
FIG. 25 is a sectional view of the present 2-L spine plate with various ones of the present bone screws of FIG. 24 taken along line 25-25 thereof.
Figure 26:
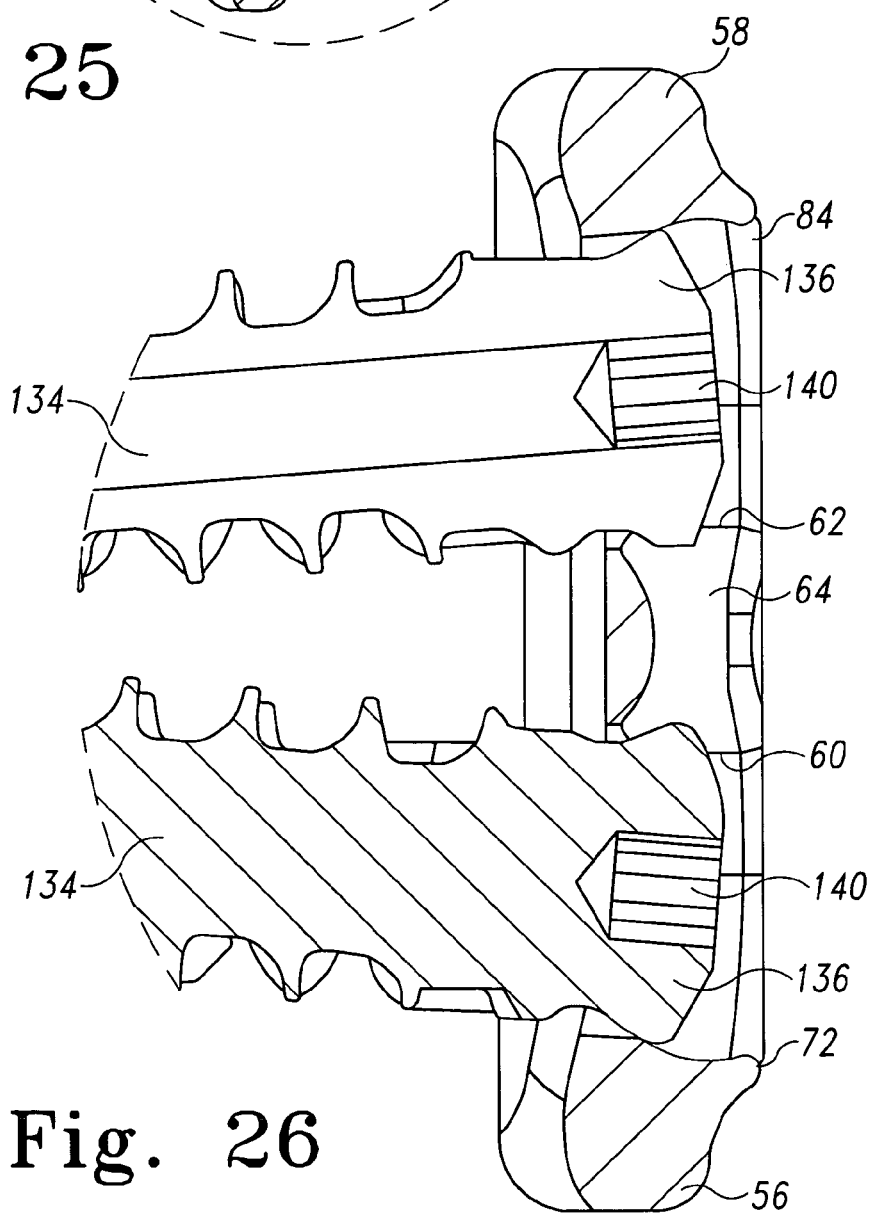
FIG. 26 is an enlarged portion of the sectional view of FIG. 25 taken along circle 26-26 thereof.

The middle section 14 has a first bone screw bore 60 formed in the side boss 56. The first bone screw bore 60 is configured to accommodate a bone screw such as described and/or shown herein. Moreover, as best seen in FIGS. 7 and 11, the first bone screw bore 60 is configured as a cylindrical hole having an arcuate lip 72 formed around a majority of the annular rim of the bore 60. The lip 72 forms an undercut 74 for the bone screw to "snap" into in order to retain the bone screw into the bore 60 when so implanted (see, e.g. FIG. 10). The bore 60 has sidewalls that are spherical and configured to provide a ten degree (10°) angulation range in the medial-lateral direction for a bone screw (see, e.g. FIGS. 25 and 26).

Figure 24:
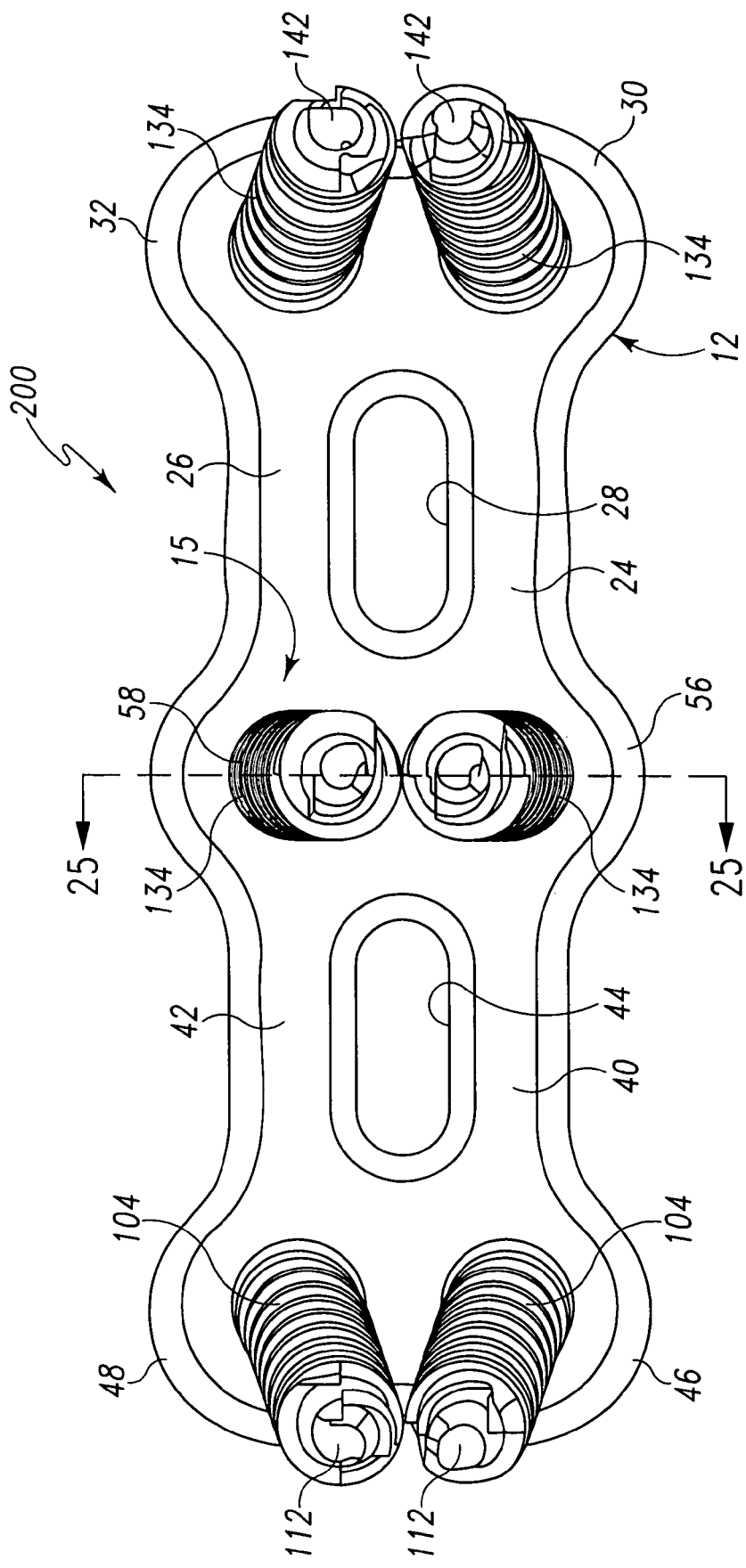
FIG. 24 is a posterior plan view of the present 2-L spine plate with various ones of the present bone screws of FIG. 22.

A second bone screw bore 62 is formed in the side boss 58 of the middle section 14. The second screw bore 62 is configured to accommodate a bone screw such as described and/or shown herein. The second bone screw bore 62 is configured as a cylindrical hole having an arcuate lip 84 formed around a majority of the annular rim of the bore 62. The lip 84 forms an undercut in like manner to undercut 74 of bore 60, for the bone screw to "snap" into in order to retain the bone screw into the bore 62 when so implanted. The bore 62 has sidewalls that are spherical and configured to provide a ten degree (10°) angulation range in the medial-lateral direction for a bone screw (see, e.g. FIGS. 25 and 26). As can be discerned in FIGS. 24, 25 and 26, the bone screw bore 60 provides angulation in a medial direction (inwards) from a longitudinal axis of the bone screw therein, while the bone screw bore 62 provides angulation in a medial direction (inwards) from a longitudinal axis of the bone screw therein.

A relief area, trough, channel or the like 64 is provided in the anterior side 13 of the plate body 12 between the first and second bores 60 and 62 of the middle section 14. The relief area 64 is preferably, but not necessarily, hour-glass shaped (see, e.g. FIG. 5) having ends that open into or provide communication with the respective first and second bores 60 and 62. As detailed in FIG. 12 with respect to the bone screw bore 52 wherein the relief area thereof is labeled 54, the relief area is configured to allow the bone screw to displace within the screw pockets when entering the bore. The relief area also is used to remove the bone screw by placing an instrument in the hole of the relief area and splaying open the screw holes.

Figure 22:
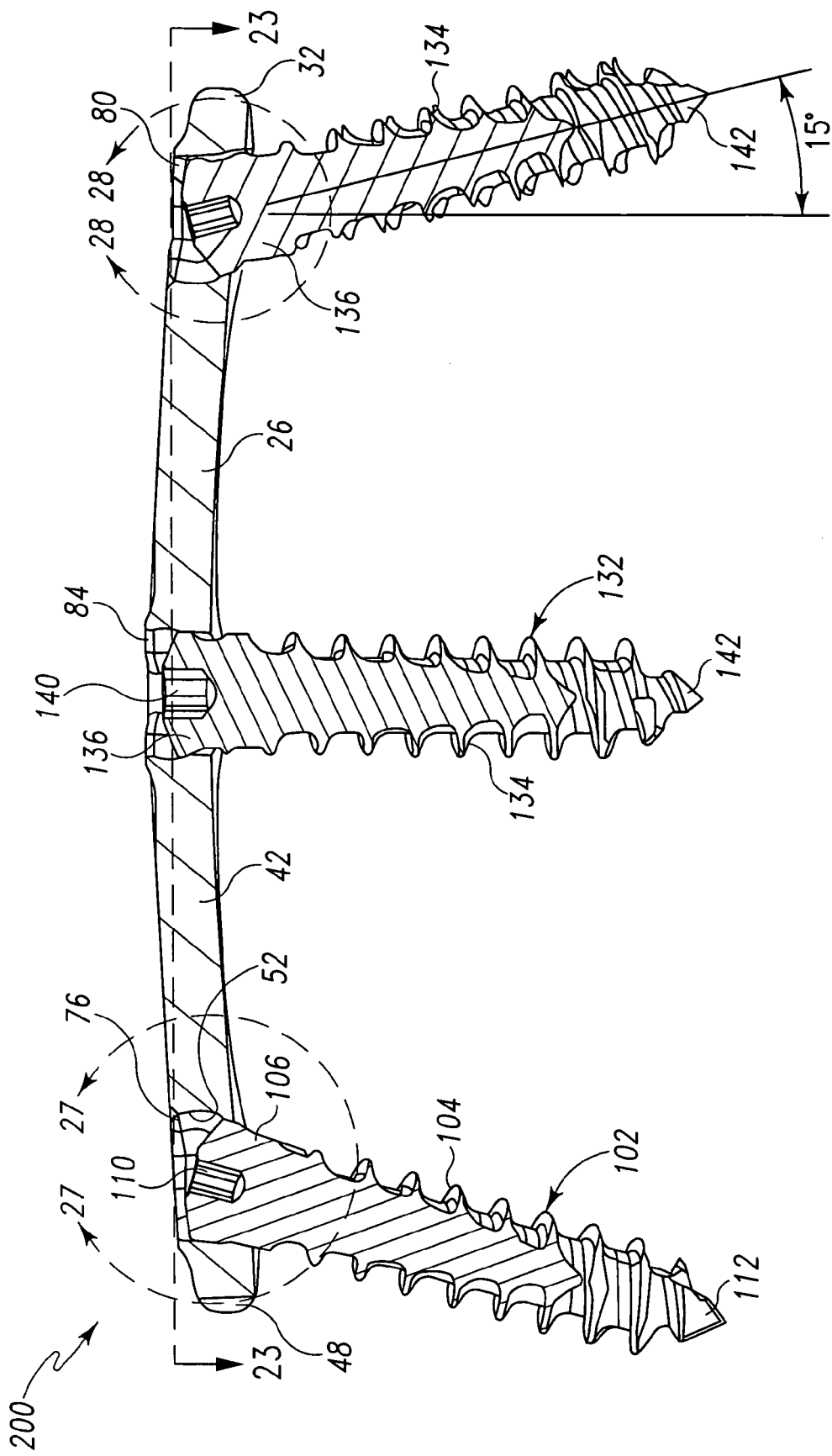
FIG. 22 is a sectional view of the 2-L spine plate with various ones of the present bone screws situated therein of FIG. 23 taken along line 22-22 thereof.

The first end 18 has a first bone screw bore 34 formed in the first boss 32. The first bone screw bore 34 is configured to accommodate a bone screw such as described and/or shown herein. Moreover, as best seen in FIGS. 7 and 10, the first bone screw bore 34 is configured as a cylindrical hole having an arcuate lip 68 formed around a majority of the annular rim of the bore 34. The lip 68 forms an undercut 70 for the bone screw to "snap" into in order to retain the bone screw into the bore 34 when so implanted. The bore 34 has sidewalls that are spherical and configured to provide bone screw angulation. The bore 34 is configured to provide a thirty degree (30°) angulation range in the cephalad-caudal direction for a bone screw (see, e.g. FIGS. 22 and 24).

The first end 18 also has a second bone screw bore 36 formed in the second boss 34. The second bone screw bore 36 is configured to accommodate a bone screw such as described and/or shown herein. The second first bone screw bore 36 is configured as a cylindrical hole having an arcuate lip 80 formed around a majority of the annular rim of the bore 36. The lip 80 forms an undercut, in like manner to undercut 70 of bore 34, for the bone screw to "snap" into in order to retain the bone screw into the bore 36 when so implanted. The bore 36 has sidewalls that are spherical and configured to provide bone screw angulation. The bore 34 is configured to provide a thirty degree (30°) angulation range in the cephalad-caudal direction for a bone screw (see, e.g. FIGS. 22 and 24). As can be discerned in FIGS. 24, 25 and 26, the bone screw bore 34 provides angulation in a medial direction (inwards) from a longitudinal axis of the bone screw therein, while the bone screw bore 36 provides angulation in a medial direction (inwards) from a longitudinal axis of the bone screw therein.

A relief area, trough, channel or the like 38 is provided in the anterior side 13 of the plate body 12 between the first and second bores 34 and 36 of the first end 18. The relief area 38 is preferably, but not necessarily, hour-glass shaped (see, e.g. FIG. 5) having ends that open into or provide communication with the respective first and second bores 34 and 36. As detailed in FIG. 12 with respect to the bone screw bore 52 wherein the relief area thereof is labeled 54, the relief area is configured to allow the bone screw to displace within the screw pockets when entering the bore. The relief area also is used to remove the bone screw by placing an instrument in the hole of the relief area and splaying open the screw holes.

The second end 22 of the body 12 of the spine plate 10 has a first bone screw bore 50 formed in the first boss 46 of the second end plate 22. The first bone screw bore 50 is configured to accommodate a bone screw such as described and/or shown herein. Moreover, the first bone screw bore 50 is configured as a cylindrical hole having an arcuate lip 88 formed around a majority of the annular rim of the bore 50. The lip 88 forms an undercut, in like manner to undercut 70 of bore 34, for the bone screw to "snap" into in order to retain the bone screw into the bore 50 when so implanted. Again, in like manner to the bore 34 but configured opposite thereto, the bore 50 has sidewalls that are spherical and configured to provide bone screw angulation. The bore 50 is configured to provide a thirty degree (30°) angulation range in the cephalad-caudal direction for a bone screw but opposite for those of the first end 18 (see, e.g. FIGS. 22 and 24).

The second end 22 of the body 12 of the spine plate 10 has a second bone screw bore 52 formed in the second boss 34 of the second end plate 22. The second bone screw bore 52 is configured to accommodate a bone screw such as described and/or shown herein. Moreover, the second first bone screw bore 52 is configured as a cylindrical hole having an arcuate lip 76 formed around a majority of the annular rim of the bore 52. The lip 76 forms an undercut 78 (see FIGS. 7 and 12) for the bone screw to "snap" into in order to retain the bone screw into the bore 52 when so implanted. The bore 52 has sidewalls that are spherical and configured to provide bone screw angulation. The bore 52 is configured to provide a thirty degree (30°) angulation range in the cephalad-caudal direction for a bone screw but opposite to that of the first end 18 (see, e.g. FIGS. 22 and 24).

Figure 12:
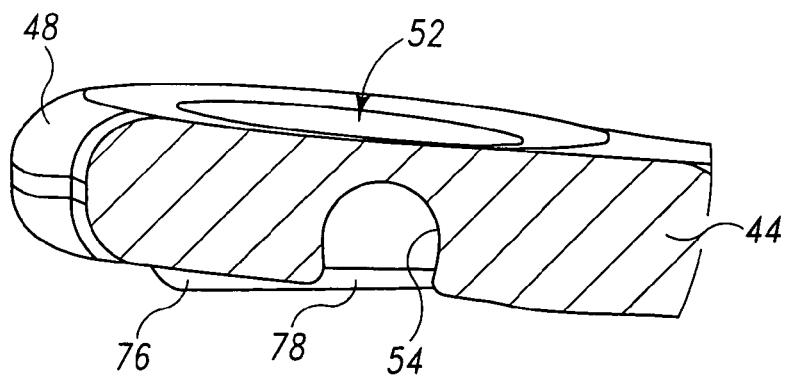
FIG. 12 is an enlarged portion of the sectional view of FIG. 6 taken along circle 12-12 thereof.

A relief area, trough, channel or the like 54 is provided in the anterior side 13 of the plate body 12 between the first and second bores 50 and 52 of the second end 22 (see, e.g. FIG. 12). The relief area 54 is preferably, but not necessarily, hour-glass shaped having ends that open into or provide communication with the respective first and second bores 50 and 52. As detailed in FIG. 12, the relief area is configured to allow the bone screw to displace within the screw pockets when entering the bore. The relief area also is used to remove the bone screw by placing an instrument in the hole of the relief area and splaying open the screw holes.

The bone screw bores or screw pockets (as defined by their geometry and/or configuration) may have a fixed or pre-disposed angulation rather than provide for a variable angulation as hereinbefore described. This would allow positioning of a received bone screw at the fixed or pre-disposed angle. This may be particularly true for the cephelad-caudel screw pockets.

Figure 14:
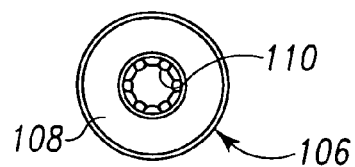
FIG. 14 is an end view of the fixed angle bone screw of FIG. 13 taken along line 14-14 thereof.
Figure 13:
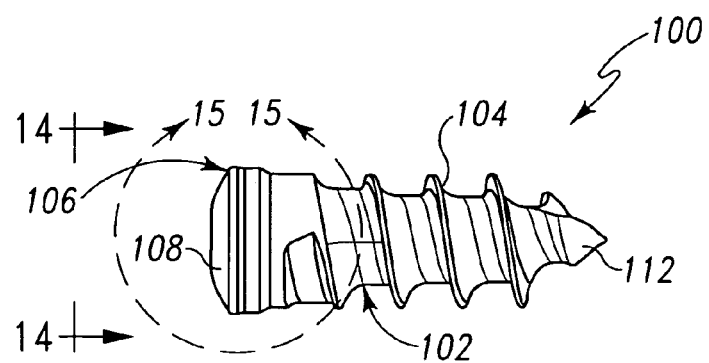
FIG. 13 is a side view of an exemplary fixed angle bone screw fashioned in accordance with the present principles.
Figure 15:
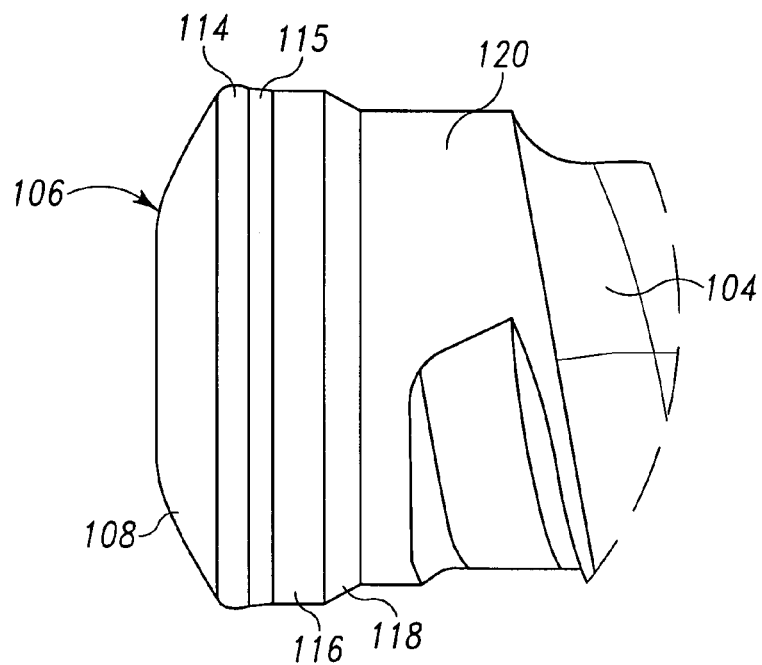
FIG. 15 is an enlarged portion of the fixed angle bone screw of FIG. 13 taken along circle 15-15 thereof.

Referring now to FIGS. 13-15, there is depicted an exemplary embodiment of a fixed angle bone screw, generally designated 100, that may be used with the present plate 10. The fixed angle bone screw 100 is characterized by a body 102 fashioned from a suitable biocompatible material such as titanium, stainless steel, alloys thereof, and the like. The body 102 has a shank 104 extending from a head 106. The shank 104 is in the form of an auger having a tip 112 and helical threads on the outer periphery thereof. The head 106 extends from the end of the shank 104 distal the tip 112. The head 106 includes an upper annular tapered area 108 that terminates in a socket 110. The socket 110 is provided on the longitudinal axis of the bone screw 100 and particularly the shank 104 and may be in the form of a hexalobe, or similar, drive or otherwise. The periphery of the head 106 is essentially annular.

Figure 27:
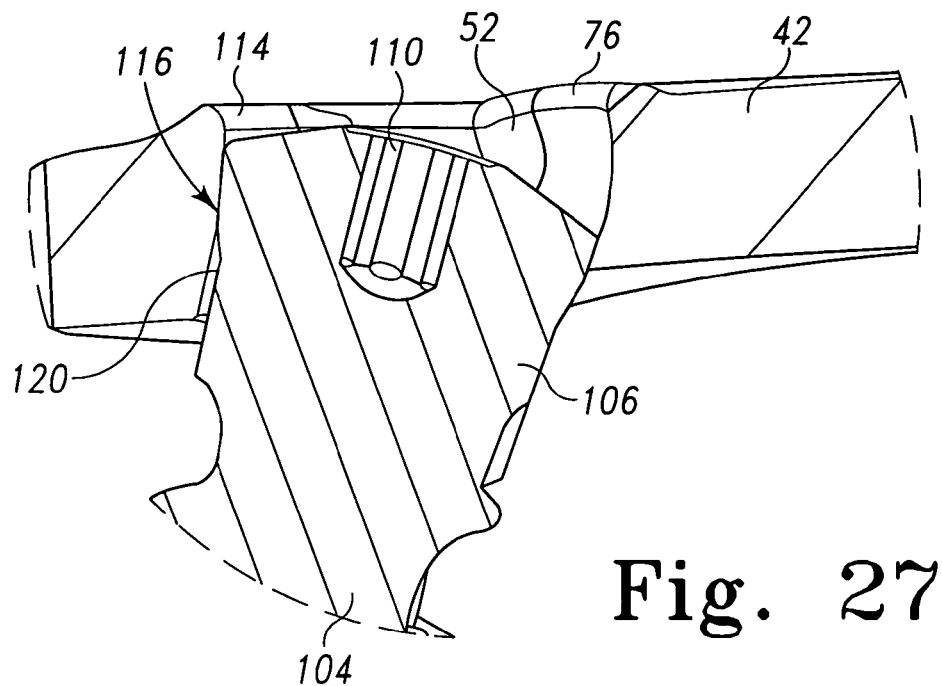
FIG. 27 is an enlarged portion of the sectional view of FIG. 22 taken along circle 27-27 thereof.

Referring to FIG. 15, the fixed angle screw head 106 includes a peripheral lip 114 that cooperates with a lip and undercut of a bone screw bore of the plate 10 as described herein in order to provide a snap feature between the bone screw bore configuration of the plate and the bone screw. Thus, as the bone screw 100 is received into a bone screw bore of the plate the peripheral lip 114 of the bone screw 100 axially passes the lip of the bone screw bore (see, e.g. FIG. 27) to snap into place in the undercut. Axial to the peripheral lip 114 is a transition area 115 that axially tapers from and helps define the peripheral lip 114 to an angulation area 116. The angulation area 116 of the fixed angle bone screw acts within the bone screw bore to prevent angulation once received therein. As particularly shown in FIG. 27, the larger diameter of the angulation area 116 prevents angulation of the bone screw in the bone screw bore (screw pocket) as the angulation area 116 meets the spherical walls of the screw pocket. Thus, once the boring angle of the fixed angle bone screw 100 is set, the angulation area 116 prevents further angulation through interaction with the geometry of the screw pocket. A second transition area 118 axially extends from the angulation area 116 to a shaft head 120. The fixed angle screw 100 may be used in any one of the bone screw bores of the plate 10.

Figure 17:
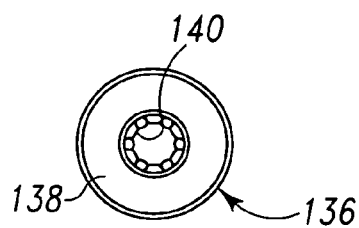
FIG. 17 is an end view of the variable angle bone screw of FIG. 16 taken along line 17-17 thereof.
Figure 16:
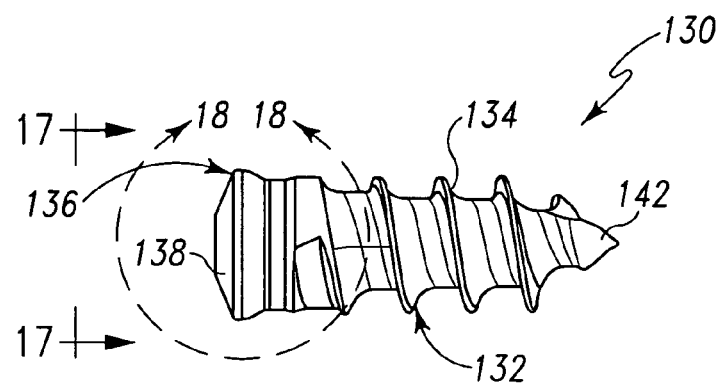
FIG. 16 is a side view of an exemplary variable angle bone screw fashioned in accordance with the present principles.
Figure 18:
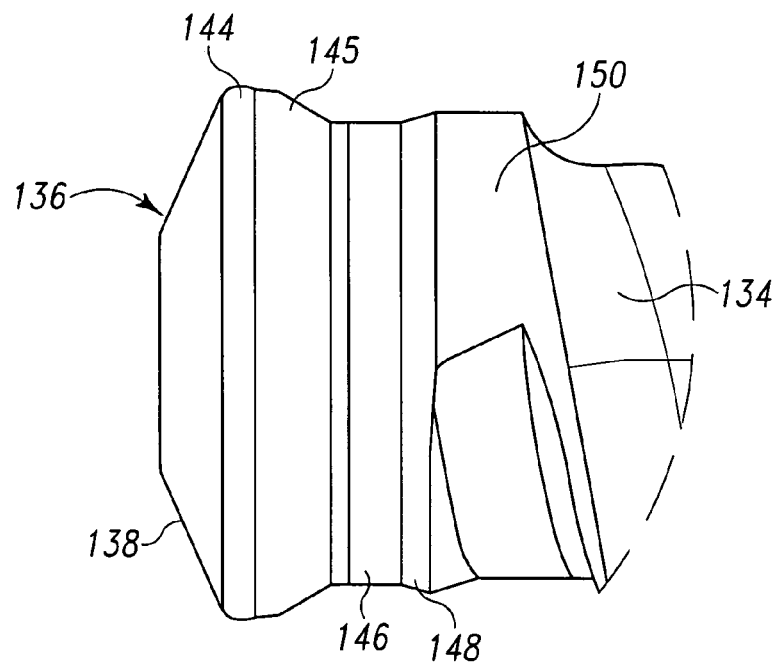
FIG. 18 is an enlarged portion of the variable angle bone screw of FIG. 16 taken along circle 18-18 thereof.

Referring now to FIGS. 16-18, there is depicted an exemplary embodiment of a variable angle bone screw, generally designated 130, that may be used with the present plate 10. The variable angle bone screw 130 is characterized by a body 132 fashioned from a suitable biocompatible material such as titanium, stainless steel, alloys thereof, and the like. The body 132 has a shank 134 extending from a head 136. The shank 134 is in the form of an auger having a tip 142 and helical threads on the outer periphery thereof. The head 136 extends from the end of the shank 134 distal the tip 142. The head 136 includes an upper annular tapered area 138 that terminates in a socket 140. The socket 140 is provided on the longitudinal axis of the bone screw 130 and particularly the shank 134 and may be in the form of a hexalobe drive or otherwise. The periphery of the head 136 is essentially annular.

Figure 28:
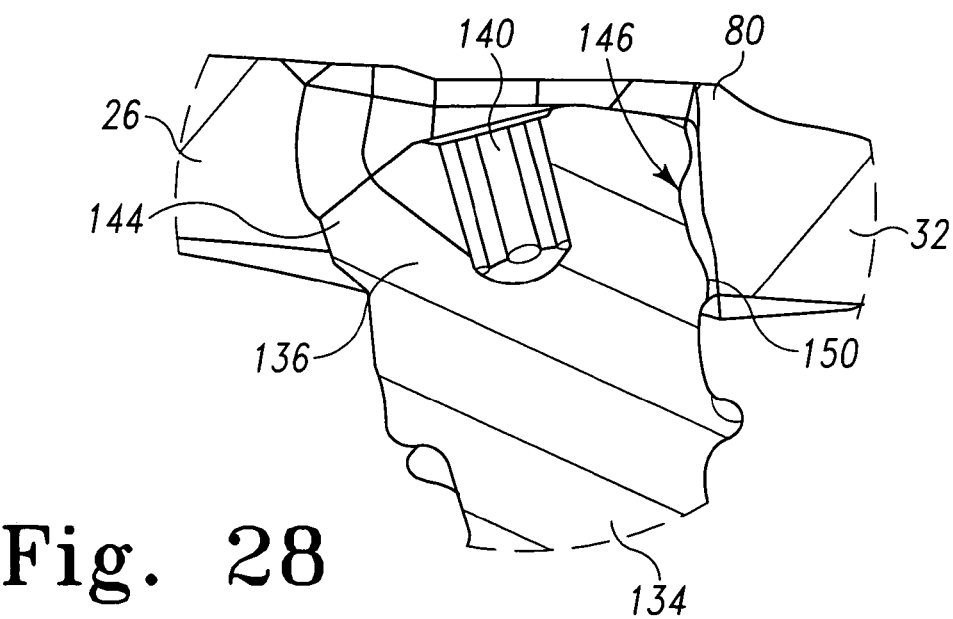
FIG. 28 is an enlarged portion of the sectional view of FIG. 22 taken along circle 28-28 thereof.

Referring to FIG. 18, the variable angle screw head 136 includes a peripheral lip 144 that cooperates with a lip and undercut of a bone screw bore of the plate 10 as described herein in order to provide a snap feature between the bone screw bore configuration of the plate and the bone screw. Thus, as the bone screw 130 is received into a bone screw bore of the plate the peripheral lip 144 of the bone screw 130 axially passes the lip of the bone screw bore (see, e.g. FIG. 28) to snap into place in the undercut. Axial to the peripheral lip 144 is a transition area 145 that axially tapers from and helps define the peripheral lip 144 to an angulation area 146. The angulation area 146 of the variable angle bone screw acts within the bone screw bore to allow angulation once received therein. As particularly shown in FIG. 28, the smaller or reduced diameter of the angulation area 146 allows angulation of the bone screw in the bone screw bore (screw pocket) as the angulation area 146 meets the spherical walls of the screw pocket. Thus, once the boring angle of the variable angle bone screw 130 is set, the angulation area 146 allows further angulation via the geometry of the screw pocket. A second transition area 148 axially extends from the angulation area 146 to a shaft head 150. The variable angle screw 130 may be used in any one of the bone screw bores of the plate 10. Such variable angle screws 130 are shown in the bone screw bores 60 and 62 of the middle section 14 (see, e.g. FIGS. 22, 25 and 26).

Figure 20:
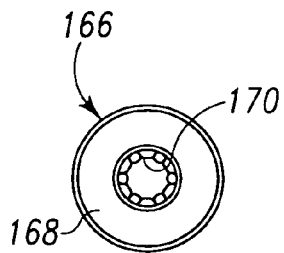
FIG. 20 is an end view of the emergency bone screw of FIG. 19 taken along line 20-20 thereof.
Figure 19:
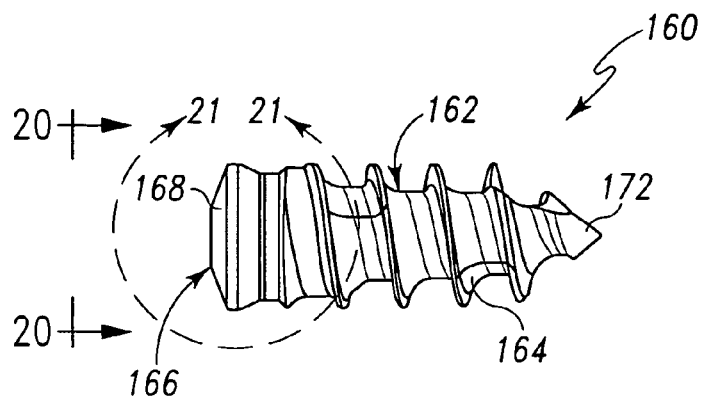
FIG. 19 is a side view of an emergency (variable) bone screw fashioned in accordance with the present principles.
Figure 21:
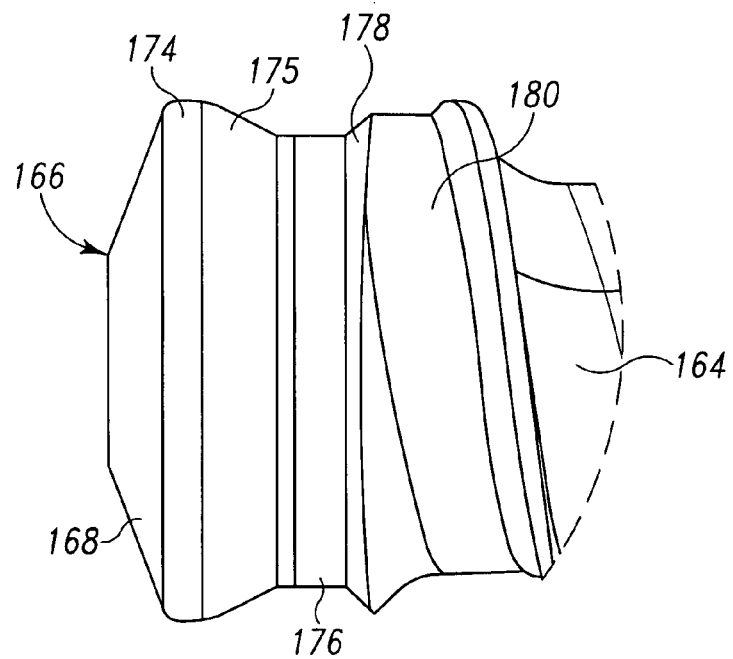
FIG. 21 is an enlarged portion of the emergency bone screw of FIG. 19 taken along circle 21-21 thereof.

Referring now to FIGS. 19-21, there is depicted an exemplary embodiment of an emergency (variable) bone screw, generally designated 160, that may be used with the present plate 10. The emergency bone screw 160 is characterized by a body 162 fashioned from a suitable biocompatible material such as titanium, stainless steel, alloys thereof, and the like. The body 162 has a shank 164 extending from a head 166. The shank 164 is in the form of an auger having a tip 172 and helical threads on the outer periphery thereof. The head 166 extends from the end of the shank 164 distal the tip 172. The head 166 includes an upper annular tapered area 168 that terminates in a socket 170. The socket 170 is provided on the longitudinal axis of the bone screw 160 and particularly the shank 164 and may be in the form of a hexalobe drive or otherwise. The periphery of the head 166 is essentially annular.

Referring to FIG. 21, the emergency screw head 166 includes a peripheral lip 174 that cooperates with a lip and undercut of a bone screw bore of the plate 10 as described herein in order to provide a snap feature between the bone screw bore configuration of the plate and the bone screw. Thus, as the bone screw 160 is received into a bone screw bore of the plate the peripheral lip 174 of the bone screw 160 axially passes the lip of the bone screw bore, such as previously described, to snap into place in the undercut. Axial to the peripheral lip 174 is an elongated transition area 175 that axially tapers from and helps define the peripheral lip 174 to an angulation area 176. The angulation area 176 of the emergency bone screw 160 acts within the bone screw bore to allow angulation once received therein. This is similar to that shown in FIG. 28 as described above with respect to variable angle bone screw 130. A second transition area 178 radially outwardly tapers from the angulation area 176 to an oversized shaft head 180. The emergency screw 160 may be used in any one of the bone screw bores of the plate 10. The helical threads of the emergency bone screw 160 are slightly larger in diameter than fixed or variable screws.

Figure 23:
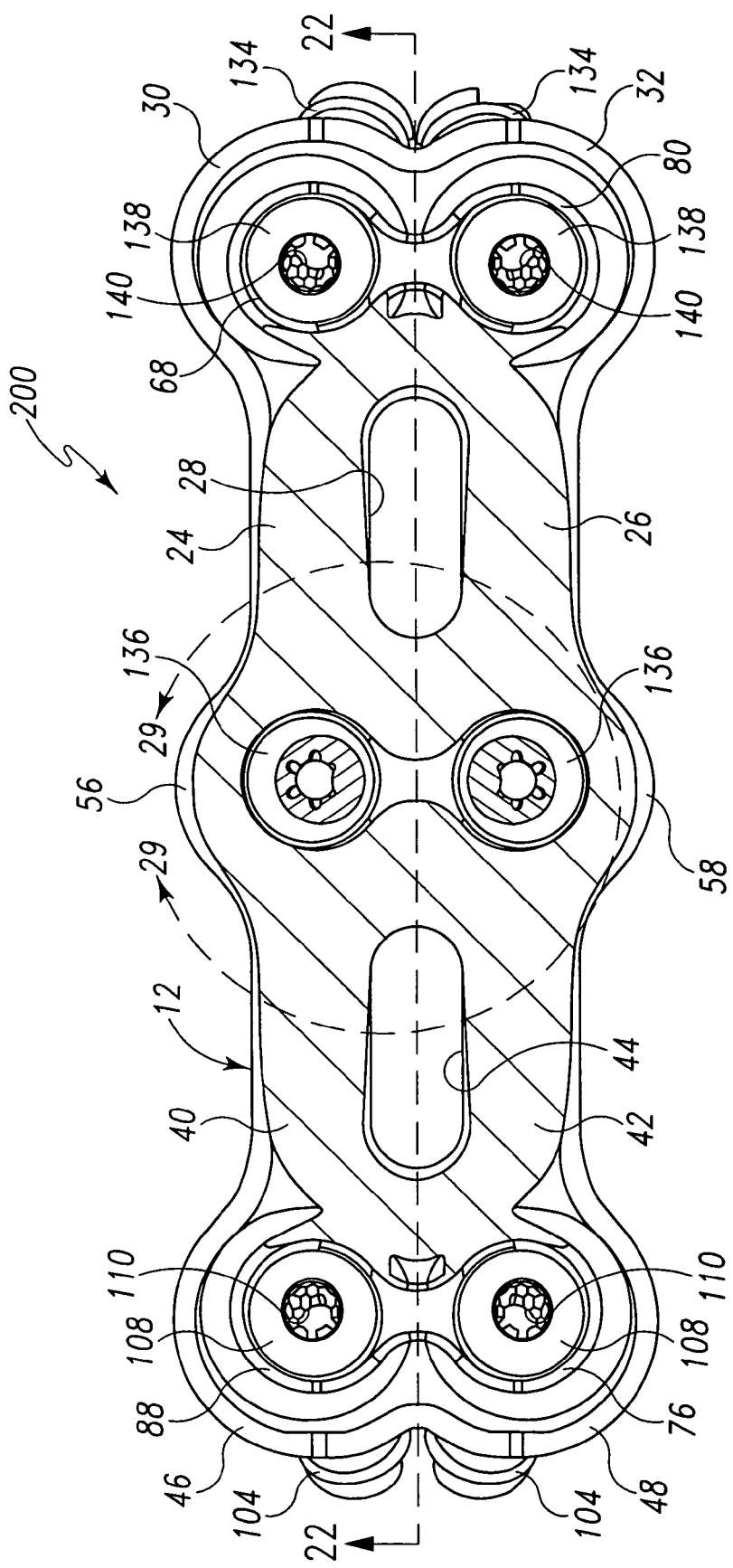
FIG. 23 is a sectional view of the present 2-L spine plate with various ones of the present bone screws of FIG. 22 taken along line 23-23 thereof.
Figure 29:
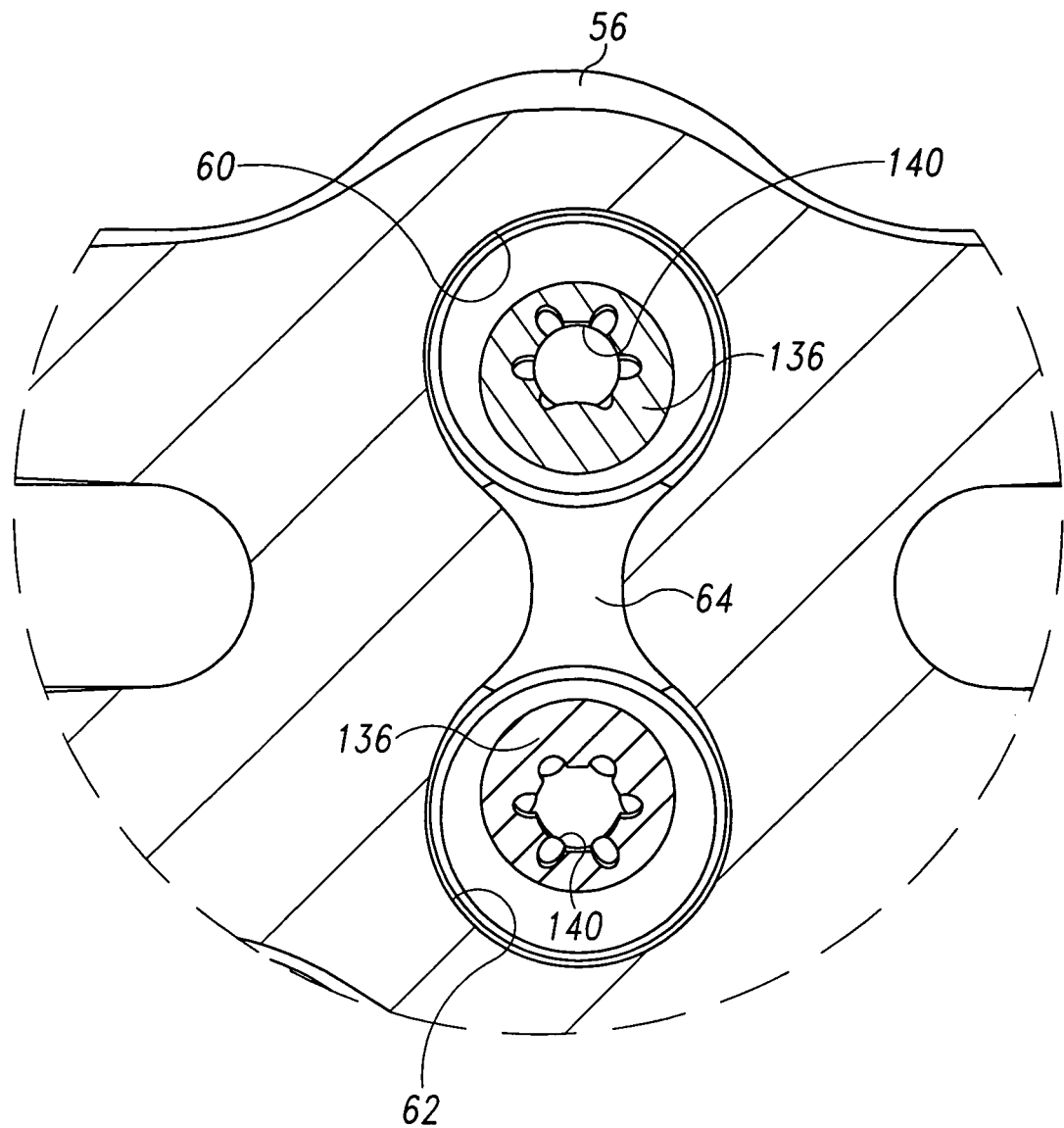
FIG. 29 is an enlarged portion of the sectional view of FIG. 23 taken along circle 29-29 thereof.

Reference is now made to FIGS. 23 and 29. When bone screws are installed in the bone screw bores of the middle section 14, the axis of the bone screws are at a centroid of the screw pocket.

It should be appreciated that a single level (1-L) spine plate has first and second ends each having first and second bone screw bores and a single neck section. A two level (2-L) spine plate has a middle section having first and second bone screw bores, first and second necks extending from each side of the middle section and each having an elongated window, a first end at the first neck distal the middle section and having first and second bone screw bores, and a second end at the second neck distal the middle section and having first and second bone screw bores. A three level (3-L) spine plate has two middle sections connected by a middle neck, then a neck and end section like the 2-L spine plate on an end of the two middle sections. This continues for higher level spine plates.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spine plate comprising:
a plate having a body defining a posterior side, an anterior side, a first end and a second end;
a first bone screw bore at the first end of the plate;
a monolithically formed first lip on the body of the plate and defining the first bone screw bore and located adjacent the anterior side to form a first undercut facing the posterior side, the first undercut configured to contact a first bone screw to retain the first bone screw at a first determinative position relative to the body in a snap engagement directly between the first lip on the spine plate and the first bone screw, wherein the first lip and first undercut allow angular movement of the first bone screw;
a second bone screw bore at the second end of the plate;
a monolithically formed second lip on the body of the plate and defining the second bone screw bore and located adjacent the anterior side to form a second undercut facing the posterior side, the second undercut configured to contact a second bone screw to retain the second bone screw at a second determinative position relative to the body in a snap engagement directly between the second lip on the plate and the second bone screw, wherein the second lip and the second undercut allow angular movement of the second bone screw.

2. The spine plate of claim 1, wherein:
the first determinative position comprises a first self-capture position that provides self-retention of the first bone screw in the first bone screw bore relative to the body solely by first bone screw bore geometry; and
the second determinative position comprises a second self-capture position that provides self-retention of the second bone screw in the second bone screw bore relative to the body solely by second bone screw bore geometry.

3. The spine plate of claim 2, wherein:
the first bone screw bore geometry includes the first undercut; and
the second bone screw bore geometry includes the second undercut.

4. The spine plate of claim 3, wherein:
the first undercut cooperates with the first lip of the first bone screw; and
the second undercut cooperates with the second lip of the second bone screw.

5. The spine plate of claim 1, wherein:
the first determinative position comprises a first limited angulation orientation of the first bone screw relative to the body; and
the second determinative position comprises a second limited angulation orientation of the second bone screw relative to the body.

6. The spine plate of claim 5, wherein:
the first limited angulation orientation of the first bone screw is relative to the cephalad to caudal direction of the body when the body is implanted on a human spine; and
the second limited angulation orientation of the second bone screw is relative to the cephalad to caudal direction of the body when the body is implanted on a human spine.

7. The spine plate of claim 1, wherein:
the body defines a middle segment between the first end and the second end; and
further comprising a third bone screw bore at the middle segment and configured to cooperate with a third bone screw to retain the third bone screw at a third determinative position relative to the body.

8. The spine plate of claim 7, wherein:
the third determinative position comprises a third limited angulation orientation of the third bone screw relative to the body.

9. The spine plate of claim 8, wherein the third limited angulation orientation of the third bone screw bore is relative to the medial to lateral direction of the body when the body is implanted on a human spine.

10. The spine plate of claim 1, wherein:
the first determinative position comprises a first range of angulation orientations of the first bone screw relative to the body; and
the second determinative position comprises a second range of angulation orientations of the second bone screw relative to the body.

11. The spine plate of claim 10, wherein:
the first range of angulation orientations is relative to the cephalad to caudal direction of the body when the body is implanted on a human spine; and
the second range of angulation orientations is relative to the cephalad to caudal direction of the body when the body is implanted on a human spine.

12. The spine plate of claim 11, wherein:
the first range of angulation orientations is 0° to 30° relative to the cephalad to caudal direction; and
the second range of angulation orientations is 0° to 30° relative to the cephalad to caudal direction.

13. The spine plate of claim 10, wherein:
the body defines a middle segment between the first end and the second end; and
further comprising a third bone screw bore at the middle segment and configured to cooperate with a third bone screw to retain the third bone screw at a third determinative position relative to the body.

14. The spine plate of claim 13, wherein:
the third determinative position comprises a third range of angulation orientations of the third bone screw relative to the body.

15. The spine plate of claim 14, wherein the third range of angulation orientations of the third bone screw bore is relative to the medial to lateral direction of the body when the body is implanted on a human spine.

16. The spine plate of claim 15, wherein the third range of angulation orientations is 0° to 10° relative to the medial to lateral direction.

17. The spine plate of claim 1, wherein:
the first determinative position allows setting of a first angulation orientation of the first bore screw but prohibits further angulation of the first bone screw once set; and
the second determinative position allows setting of a second angulation orientation of the second bone screw but prohibits further angulation of the second bone screw once set.

18. The spine plate of claim 1, wherein:
the first bone screw bore is configured as a first spherically cupped shape and the first determinative position comprises retention of the first bone screw in a centroid of the first bone screw bore when the first bone screw is installed in the first bone screw bore; and
the second bone screw bore is configured as a second spherically cupped shape and the second determinative position comprises retention of the second bone screw in a centroid of the second bone screw bore when the second bone screw is installed in the second bone screw bore.

19. A spine device comprising:
a plate having a body defining a posterior side, an anterior side, a first end and a second end;
a plurality of bone screws, each having a shank and a head, each head having a first lip and an angulation area location between the first lip and the shank;
a first plurality of bone screw bores extending through the body of the plate from the anterior side to the posterior side, each one of the first plurality of bone screw bores defined by a sidewall and a monolithically formed second lip located adjacent the anterior side of the body that forms an undercut facing the posterior side;
wherein the first lip and angulation area of the bone screws directly engage the sidewall and the second lip of the bone screw bores;
wherein the second lip and the undercut allow angular movement of the bone screw constrained therein;
wherein the first lip on the bone screws has a diameter greater than a diameter of the first lip to retain the bone screw at a determinative orientation relative to the body.

20. The spine device of claim 19, wherein the angulation area has a diameter configured to engage the sidewall of the bore and prevent angulation of the bone screw.

21. The spine device of claim 19, wherein the angulation area has a diameter configured to engage the sidewall of the bore and allow angulation of the bone screw.

22. The spine device of claim 19, wherein each bone screw bores have an egress opening in the body of the plate adjacent to the posterior side that is axially offset from an opening adjacent the anterior side.

23. A spinal device comprising:
(i) a plate having a posterior side, an anterior side, a first end, a second end, and a plurality of bone screw bores extending through the plate from the anterior side to the posterior side, each one of the plurality of bone screw bores comprising:
a monolithically formed lip located adjacent the anterior side of the body;
a sidewall extending into the bore from the posterior side of the plate;
a non-threaded undercut facing the posterior side and located between the lip and the sidewall;

(ii) a fixed angle bone screw for use with the plate and configured to prevent angulation of the fixed angle bone screw once received in the plate, the fixed angle bone screw comprising:
a shank;
a head; and
a shaft head between the shank and the head;
wherein the head having a lip and an angulation area located between the lip and the shank head, the angulation area having a diameter smaller than a diameter of the lip and larger than a diameter of the shaft head;
wherein when the fixed angle bone screw is engaged in direct contact with one of the plurality of bone screw bores, relative diameters of the fixed angle bone screw and the plate fixes the angle between the fixed angle bone screw and a centroid of the bone screw bore;

(iii) a variable angle bone screw for use with the plate and configured to allow angulation of the fixed angle bone screw once received in the plate, the variable angle bone screw comprising:
a shank;
a head; and
a shaft head between the shank and the head;
wherein the head having a lip, and an angulation area located between the lip and the shank head, the angulation area having a diameter smaller than a diameter of the lip and smaller than a diameter of the shaft head;
wherein when the variable angle bone screw is engaged in direct contact with one of the plurality of bone screw bores, relative diameters of the angulation area of the variable angle bone screw and the bore allow for further angulation of the variable angle bone screw relative to a centroid of the bone screw bore, and wherein the second lip of the plurality of bone screw bores allow angular movement of the variable angle bone screw;

(iv) wherein the diameter of the lip of the first bone screw and the diameter of the lip of the second bone screw both have a diameter greater than a diameter of the lip on any of the plurality of bone screw bores to provide a direct snap engagement between the plate and the first or second bone screws.

\* \* \* \* \*